(12) United States Patent
Cohen et al.

(10) Patent No.: US 9,737,254 B2
(45) Date of Patent: Aug. 22, 2017

(54) PERSONAL MEDICAL TESTING HOUSING

(71) Applicants: Dan Cohen, Melville, NY (US); Austin Kahn, Melville, NY (US)

(72) Inventors: Dan Cohen, Melville, NY (US); Austin Kahn, Melville, NY (US)

(73) Assignee: NOVTEX LLC, Melville, NY (US)

( * ) Notice: Subject to any disclaimer, the term of this patent is extended or adjusted under 35 U.S.C. 154(b) by 0 days.

(21) Appl. No.: 15/161,924

(22) Filed: May 23, 2016

(65) Prior Publication Data

US 2017/0143245 A1 May 25, 2017

Related U.S. Application Data

(60) Provisional application No. 62/258,637, filed on Nov. 23, 2015.

(51) Int. Cl.
*A61B 5/151* (2006.01)
*A61B 5/157* (2006.01)
*G01N 33/487* (2006.01)

(52) U.S. Cl.
CPC ............. *A61B 5/157* (2013.01); *A61B 5/151* (2013.01); *A61B 2560/0425* (2013.01); *A61B 2562/0295* (2013.01); *G01N 33/48757* (2013.01)

(58) Field of Classification Search
None
See application file for complete search history.

(56) References Cited

U.S. PATENT DOCUMENTS

| 5,753,246 A | 5/1998 | Peters |
| 5,938,069 A | 8/1999 | Macchia |
| 5,971,941 A | 10/1999 | Simons et al. |
| 6,159,424 A * | 12/2000 | Kauhaniemi ........ A61B 5/1411 422/63 |
| 6,508,383 B2 | 1/2003 | Lidahl et al. |
| 6,540,672 B1 | 4/2003 | Simonsen et al. |

(Continued)

FOREIGN PATENT DOCUMENTS

| CN | 103190914 A | 7/2013 |
| WO | 03082091 A2 | 10/2003 |

OTHER PUBLICATIONS

International Search Report and PCT Written Opinion dated Mar. 2, 2017 issued in corresponding PCT International Application No. PCT/US16/63511.

*Primary Examiner* — Devin Henson
*Assistant Examiner* — Matthew Kremer
(74) *Attorney, Agent, or Firm* — Troutman Sanders LLP

(57) ABSTRACT

A device for facilitating the testing of a fluid sample on a test strip includes a housing containing a loading receptacle, a support member, a disposal receptacle, a lancet device and a sensor device. The loading receptacle is adapted to receive the test strip. The support member is adapted to support the test strip. The disposal receptacle is adapted to hold the test strip. The sensor device is adapted to analyze the fluid sample. The device further includes a strip control assembly that is adapted to move the test strip from a first position in the loading receptacle to a second position on the support member, and from the second position to a third position in the disposal receptacle. The device may include a sample door that provides access to the test strip in the second position wherein the test strip is operatively engaged with the sensor device.

16 Claims, 13 Drawing Sheets

(56) References Cited

U.S. PATENT DOCUMENTS

| | | | |
|---|---|---|---|
| 7,935,307 B2 | 5/2011 | Angelides | |
| 8,263,019 B2 * | 9/2012 | List | G01N 33/48757 221/232 |
| 8,657,762 B2 * | 2/2014 | Takashima | A61B 5/150022 600/583 |
| 8,934,955 B2 | 1/2015 | Schraga | |
| 8,971,982 B2 | 3/2015 | Schraga | |
| 2003/0133847 A1 * | 7/2003 | Hagen | G01N 33/48757 422/430 |
| 2003/0191415 A1 | 10/2003 | Moerman et al. | |
| 2003/0212345 A1 | 11/2003 | McAllister et al. | |
| 2007/0173739 A1 * | 7/2007 | Chan | A61B 5/1411 600/583 |
| 2008/0217353 A1 * | 9/2008 | Newman | G01N 33/48757 221/210 |
| 2010/0206751 A1 | 8/2010 | Wessel | |
| 2012/0053436 A1 * | 3/2012 | Sauers | A61B 5/14532 600/365 |
| 2012/0179185 A1 | 7/2012 | Lum | |
| 2013/0338464 A1 * | 12/2013 | Stainken | A61B 5/14532 600/365 |
| 2014/0213935 A1 | 7/2014 | Hsu et al. | |
| 2015/0144484 A1 | 5/2015 | Reynolds et al. | |

\* cited by examiner

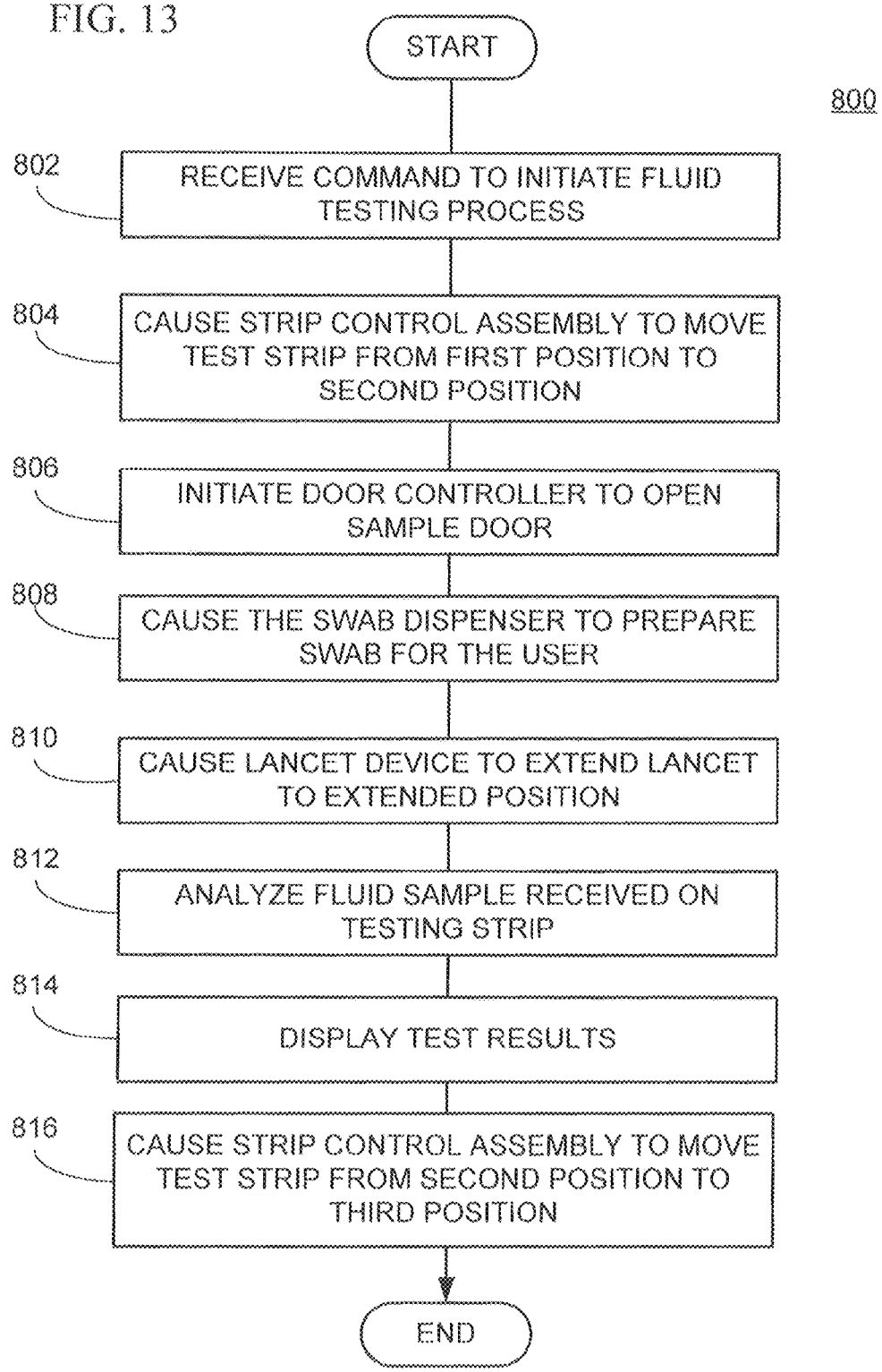

PERSONAL MEDICAL TESTING HOUSING

CROSS-REFERENCE TO RELATED APPLICATIONS

This application claims priority to U.S. Provisional Application Ser. No. 62/258,637 filed Nov. 23, 2015. This application is incorporated by reference herein in its entirety.

FIELD OF THE INVENTION

This invention relates to a device and method for personal medical testing, and in particular, a device for one-handed or hands-free blood sampling and analysis.

BACKGROUND

Millions of people around the world must track their blood sugar levels and other indicators to insure that the body is in a state of homeostasis. These people often carry a portable testing kit to test their blood sugar levels throughout the day. Such a testing kit often includes a variety of separate components that must be carried and maintained. The lack of unity between the components of the testing kit usually results in the user carrying a backpack, bag, fanny pack or other type of carrying unit to hold the separate components of the testing kit. Carrying such a bag or pack often presents a problem for the user. For example, many public events and venues prevent a user from entering with a bag or pack, or they are frowned upon, and/or go against a social norm. In addition, carrying such a bag or pack is often inconvenient for the user to handle. Such a bag or pack can also be easily misplaced or damaged.

Another problem with using a known testing kit with a variety of separate components is that these kits often require multiple hands-on steps that are unnecessary, inefficient, and unsanitary. For a diabetic that needs to test his blood sugar levels numerous times throughout a day, blood glucose analysis involves several steps that require handling several different test kit components. For example, a conventional testing method involves the user opening a testing case, opening a test strip holder, removing a single test strip from the test strip holder, removing a separate blood glucose meter from the case, inserting the single test strip into the blood glucose meter, which causes the meter to turn on, removing the separate lancet device from the testing case, loading a lancet in the lancet device, retrieving a separate alcohol swab or other cleaning agent, removing the packaging from the swab and applying the swab to the tissue area where the blood sample will be drawn, releasing the loaded lancet, pricking the tissue area with the lancet to draw the blood sample, applying the blood sample onto the test strip, and waiting for the blood glucose meter to yield a result. If a swab or cleaning agent is not available, a user may alternatively wash the tissue area with soap and water until the area is adequately cleaned.

As one can see, these steps require the physical handling of multiple devices, and components, each of which creates unnecessary inconvenience and possible sources of contamination in the process. Moreover, the process is drawn out and conspicuous, especially if the user must do it in a public or semi-public environment. Accordingly, there is a need for improved devices, systems, and methods in the areas of fluid sample testing including, but not limited to, aspects of time, easiness of use, conspicuousness, cleanliness, and accuracy, and implementations of the present disclosure are directed to this and other considerations.

SUMMARY

Briefly described, examples of the present disclosure can include device for facilitating the testing of a fluid sample, such as a blood sample, on a test strip. In some examples, for example, the device may include a housing containing a loading receptacle, a support member, a disposal receptacle, a lancet device and a sensor device. The loading receptacle is adapted to receive the test strip. The support member is adapted to support the test strip. The disposal receptacle is adapted to hold the test strip. The sensor device is adapted to analyze the fluid sample. The device further includes a strip control assembly that is adapted to move the test strip from a first position in the loading receptacle to a second position on the support member, and from the second position to a third position in the disposal receptacle. The device may include a sample door that provides access to the test strip in the second position wherein the test strip is operatively engaged with the sensor device.

In yet another aspect, a device is disclosed for facilitating the testing of a fluid sample on a test strip. The device may include a housing containing a loading receptacle adapted to receive the test strip in a first position, a support member adapted to support the test strip in a second position, a disposal receptacle adapted to hold the test strip in a third position, a lancet device, a sensor device adapted to analyze the fluid sample, and a strip control assembly including a control member, the control member disposed partially within the housing, the control member adapted to move the test strip from the first position to the second position and from the second position to the third position. The device may further include a loading door to load the test strip into the housing, a sample door in the housing to access the test strip in the second position, a disposal door in the housing to access the test strip in the third position. In operation, in the second position, the test strip is operatively engaged with the sensor device, and the test strip is accessible through the sample door to receive the fluid sample.

Further features of the disclosed design, and the advantages offered thereby, are explained in greater detail hereinafter with reference to specific examples illustrated in the accompanying drawings, wherein like elements are indicated be like reference designators.

BRIEF DESCRIPTION OF THE DRAWINGS

Reference will now be made to the accompanying FIGS., which are not necessarily drawn to scale, and which are incorporated into and constitute a portion of this disclosure, illustrate various implementations and aspects of the disclosed technology and, together with the description, serve to explain the principles of the disclosed technology. In the FIGS.:

FIG. 13 is a flow diagram of a method of using a testing device in accordance with an example implementation of the disclosed technology.

DETAILED DESCRIPTION

Some implementations of the disclosed technology will be described more fully with reference to the accompanying drawings. This disclosed technology may, however, be embodied in many different forms and should not be construed as limited to the implementations set forth herein. The components described hereinafter as making up various elements of the disclosed technology are intended to be illustrative and not restrictive. Many suitable components that would perform the same or similar functions as components described herein are intended to be embraced within the scope of the disclosed electronic devices and methods. Such other components not described herein may include, but are not limited to, for example, components developed after development of the disclosed technology.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Example implementations of the disclosed technology will now be described with reference to the accompanying FIGS.

Figure 1:
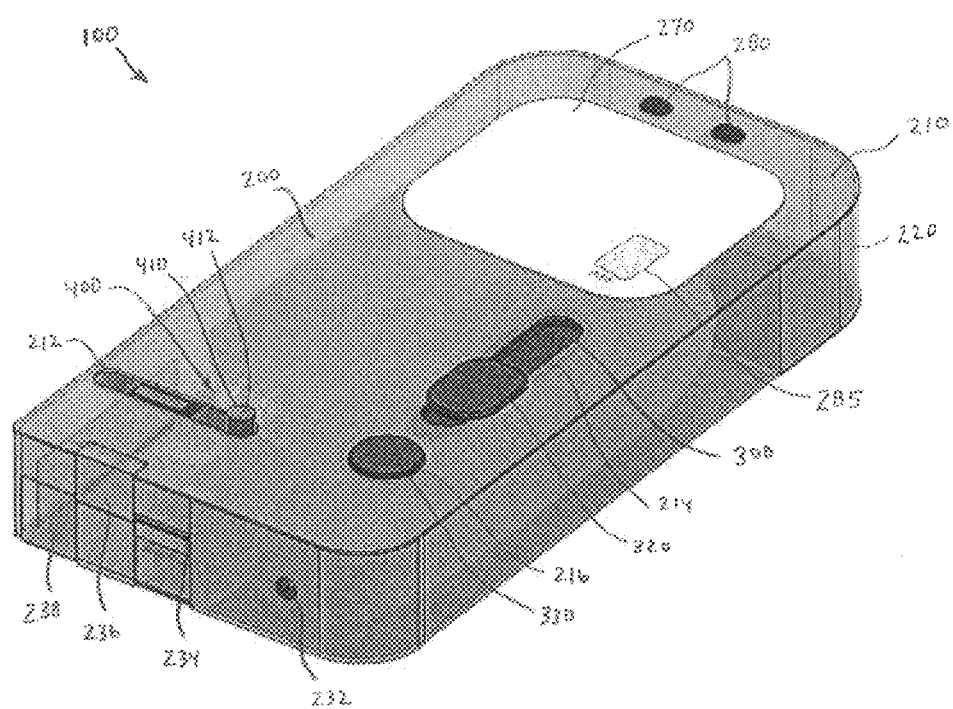
FIG. 1 is a perspective view of a fluid sample testing device in accordance with an example implementation of the disclosed technology.

FIG. 1 is a perspective view of a fluid sample testing device 100 in accordance with an example implementation of the disclosed technology. As shown in FIG. 1, the testing device 100 includes a housing 200, a lancet device 300, and a testing strip control assembly 400. The testing device 100 further includes a sensor device described in more detail in reference to later figures. To facilitate the testing of a fluid sample (e.g., a blood sample) in a single device, the lancet device 300, the sensor device, and the test strip control assembly 400 are primarily contained within the housing 200 but can be controlled by a user handling the device externally. As shown in FIG. 1, in some implementations, the housing 200 includes a top portion 210 and a bottom portion 220, which define an interior area in which the device components are primarily contained.

Once loaded with a test strip and a lancet, the testing device 100 provides a unitary, self-contained testing device that can be used to draw a fluid sample, deposit the fluid sample on a test strip contained within the testing device 100, see the results of the fluid sample analysis, and store the used test strip in a disposal area within the testing device 100 until it is convenient for the user to discard the used test strip.

The lancet device 300 includes a body 310 adapted to hold one or more lancets 340, a loading mechanism 320, and a control button 330. The body 310 is disposed within the housing 200. The loading mechanism 320 is operatively connected to the body 310, and extends outside the housing 200 through lancet charging slot 214 so that it can be actuated by a user. The loading mechanism 320 can be used to load a lancet 340 from a storage position within the body 310 to a firing position where it is ready for use.

The control button 330, or firing button, is also operatively connected to the body 310, and extends outside the housing 200 through lancet firing slot 216 so that it can be actuated by a user. When the control button 330 is pressed, the loaded lancet 340 moves axially from a retracted position within the lancet body 310 out through the lancet aperture 232 in the housing 200 to an extended position. In the extended position, the user of the testing device 100 can use the extended lancet 340 to puncture her body tissue to draw a fluid sample that can then be analyzed in the testing device 100.

The testing strip control assembly 400 includes a control member 410, or plunger, slidably disposed at least partially within a strip control slot 212 in the housing 200. The control member 410 includes a user contact portion 412 and a strip contact portion 414. The user contact portion 412 extends outside of the housing 200 through strip control slot 212 so that it can be actuated by a user. The strip contact portion 414 is contained within the housing 200 to contact a testing strip stored in the housing 200 so that it can be moved between a storage position, a sampling position and a disposal position as needed in accordance with the disclosed technology.

In some implementations, a plurality of doors are mounted in the housing 200 to provide access to the interior of the housing 200 as needed in accordance with the disclosed technology. As shown in FIG. 1, the housing 200 includes a loading door 234, a sample door 236, and a disposal door 238. These doors may be slidably or hingedly mounted to the housing 200, or in any other manner understood by one of ordinary skill in the art. The loading door 234 can be used to load testing strips into the testing device 100. The sample door 236 can be used to provide a fluid sample on a testing strip contained within the housing 200. The disposal door 238 can be used to access used testing strips contained in the housing 200 for disposal when convenient to the testing device user.

The testing device 100 also includes user interface components configured to receive input from the user and provide output information to the user. For example, in some implementations, the testing device 100 may include a display 270 and user input device 280 operatively connected to the sensor device of the testing device 100. The display 270 may include any conventional display mechanism, such as a flat panel display, a presence-sensitive display, a resistive or capacitive touch screen, projector, or any other display mechanism known to those having ordinary skill in the art. In some implementations, the display 270, in conjunction with suitable stored instructions, may be used to implement a graphical user interface displaying an application icon 285 that may be used to control a process or execute instructions, such as an automated testing process, or allow the user to provide input or data to a processor. In other implementations, the display 270 may include a display interface configured to receive or communicate with one or more external displays. As shown in FIG. 1, the user input device 280 comprises a plurality of buttons. In other implementations, the user input device 280 may include any mechanism for providing user input to the processor, including a keyboard, a mouse, a touch screen, a trackball, a directional pad, a track pad, a touch-verified track pad, a presence-sensitive track pad, a presence-sensitive display, a scroll wheel, a microphone and suitable voice recognition application, or any other means whereby a user of the device 100 may provide input or data to a processor. In some implementations, the user may utilize the user input device 280 to input data, such as a user profile, including user preferences, set testing parameters or preferences, and review stored data or test results.

Figure 2:
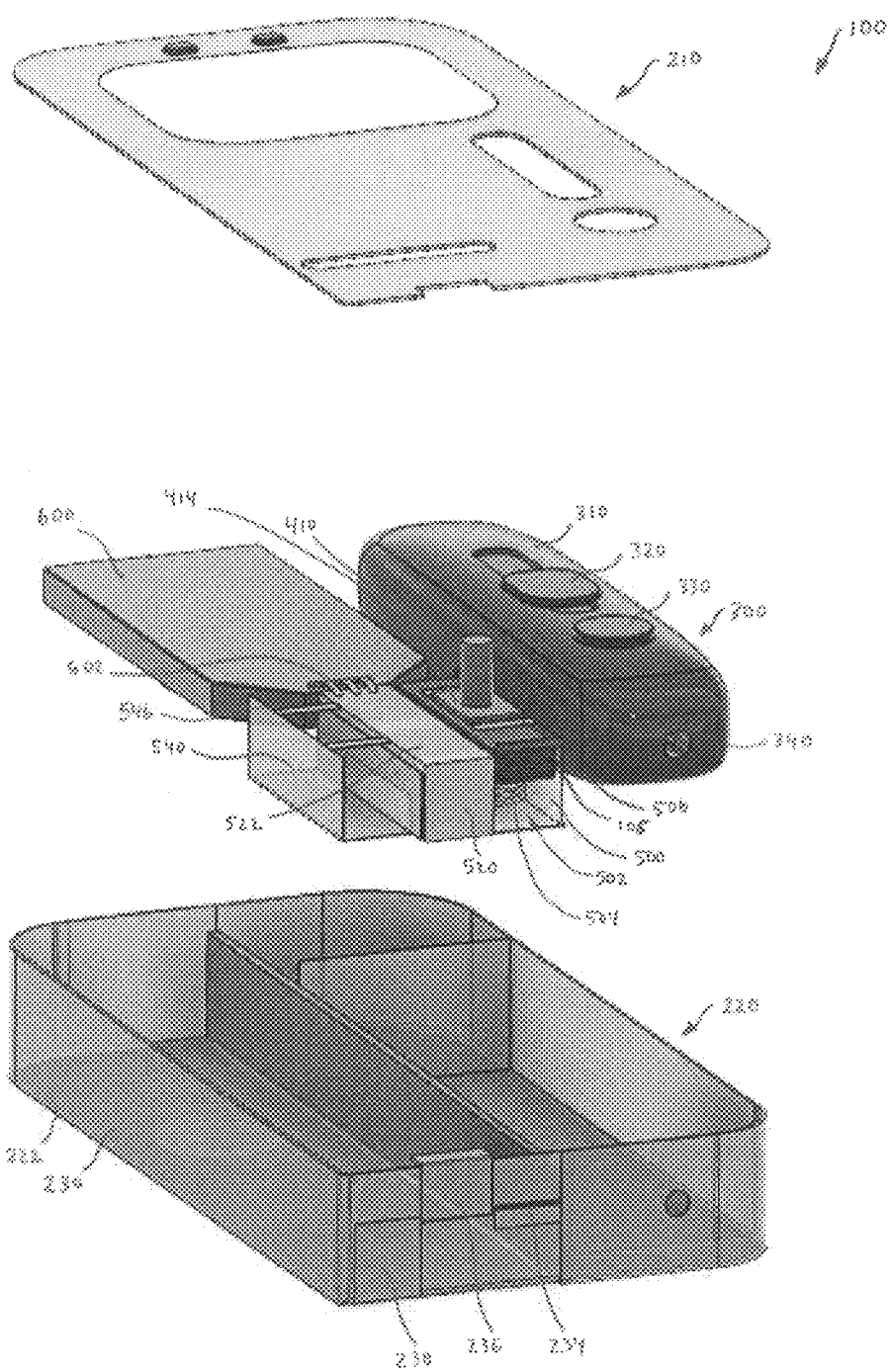
FIG. 2 is an exploded perspective view of a fluid sample device in accordance with an example implementation of the disclosed technology.

FIG. 2 is an exploded perspective view of a fluid sample device in accordance with an example implementation of the disclosed technology. Housing 200 includes a bottom 222 and at least one sidewall 230 extending upward from the bottom 222 to attach to the top portion 210 and define the interior of the housing 200. The sidewall 230 may be formed from one sidewall, or alternatively, be made up of a plurality of sidewalls.

The testing device 100 includes a loading receptacle 500 adapted to receive a plurality of test strips 106. As shown in FIG. 2, in some implementations, the test strips 106 are retained in the loading receptacle 500 between a spring mechanism 502 and a plurality of guides 506 attached to an interior wall in the housing 200. The spring mechanism 502 includes a spring means 504 mounted in the loading receptacle and connected to a moveable platform 505. In some implementations, the spring means 504 includes a compression spring that offers resistance to a compressive force applied to the platform 505 of the spring mechanism 502. When no test strips are loaded in the loading receptacle 500, the platform 505 of the spring mechanism 502 may rise up to meet and be held in place by the guides 506. As a test strip is loaded into the loading receptacle 500, the test strip slides under the guides 506 and forces the platform 505 down, which compresses the spring means 504. The spring mechanism 502 is configured to compress so that the loading receptacle 500 can receive a plurality of test strips 106, as shown in FIG. 2. In some implementations, test strips may be provided in a cartridge adapted to be loaded into the loading receptacle 500.

The strip contact portion 414 of the control member 410 is slidably disposed within the housing such that it can contact a testing strip stored in the loading receptacle 500 in a first position. The first position refers to the top positioned testing strip in the stack of testing strips 106 retained in the loading receptacle 500. As shown in FIG. 2, in some implementations, the strip contact portion 414 may be positioned over a testing strip in the first position and between the guides 506 so that the strip contact portion 414 can releasably contact the top testing strip among the plurality of loaded testing strips 106. The strip contact portion 414 may include an adhesive to releasably grip the testing strip when a user presses down on the user contact portion 412 of the control member 410, and compresses the test strip between the contact portion 414 and other testing strips 106 stacked on the platform 505 of the spring mechanism 502, or the platform 505 itself. In some implementations, the adhesive comprises a microsuction tape affixed to the contact portion 414. The control member 410 is capable of moving the top test strip in the stack from the first position to a second position over the support member 520.

The support member 520 is adapted to support an individual test strip in a sampling position. In operation, the control member 410 moves a test strip from the first position into a second position over the support member 520. In this second position, the test strip is accessible to a user of the testing device through the sample door 236 in the housing 200. The user can open the sample door 236 to access the test strip as it rests on the platform 522 of the support member 520 to provide a fluid sample on the test strip. In this regard, once the test strip is loaded into the testing device 100, the user does not need to directly handle the test strip again prior to testing. This reduces the chances of contaminating the test strip and the sample results.

In some implementations, the strip control assembly 400 includes a spring that is triggered when the control member 410 moves the testing strip into the second position on the support member 520. The spring may be configured to automatically open the sample door 236 in this position. In some implementations, the strip control assembly 400 includes a locking mechanism to temporarily hold the control member 410 in place as desired for the operation of the testing device 100, such as over the second position and over the third position. In addition, a locking mechanism may release the control member 410 when forced by the user, or for example, when the sample door 236 is closed following the provision of the fluid sample on the testing strip.

In the second position, the test strip is also arranged so that it is operatively connected to the sensor device 600 through strip contacts 602. In some implementations, the sensor device 600 comprises a glucose meter. In operation, once the user has provided the fluid sample on the test strip, the fluid sample disperses on the test strip as understood by those of ordinary skill in the art. In some implementations, the strip contacts 602 of the sensor device 600 contact the test strip and receive data as understood by those of ordinary skill in the art. For example, a test strip suitable for use with the disclosed technology may include membrane strip technology or other test strip designs known in the art for electrochemical or photometric analysis of the fluid sample. In some implementations, a test strip may include a sample receiving area with channels for directing the fluid sample to an analysis portion of the test strip, which can produce a current through electrical components configured to operatively engage with the strip contacts 602 of the sensor device 600, as will be understood by those of ordinary skill in the art.

Once the sensor device 600 completes the analysis of the fluid sample on the test strip, the user can prepare to dispose of the used test strip. Given that it is not always convenient to discard a test strip immediately following testing, the testing device 100 includes a disposal receptacle 540 to store the used test strip following testing until the user is ready to discard the used test strip.

As shown in FIG. 2, in some implementations, the disposal receptacle 540 is located adjacent to the support member 520 and adapted to receive and store used test strips until they can be discarded. Once testing is complete, using the control member 410, the user can move the used test strip over the disposal receptacle 540 into a third position. Once over the disposal receptacle 540, the user can releasably detach the used test strip from the control member 410. In some implementations, the used test strip is detached from the control member 410 by the upward movement of the control member 410 between a plurality of disposal guides 546 that restrict the upward movement of the used test strip, which forces the used test strip to separate from the contact portion 414. The used test strip is stored in the disposal receptacle 540 until the user opens the disposal door 238 in the housing and removes the used test strip or strips.

In accordance with the disclosed technology, once the test strip is loaded into the testing device 100, the user does not need to directly handle the test strip again prior to testing. This reduces the chances of contaminating the test strip and the sample results. The control member 410 is used to move the test strip between a loading (first) position, a sampling (second) position and a disposal (third) position as needed.

Figure 12:
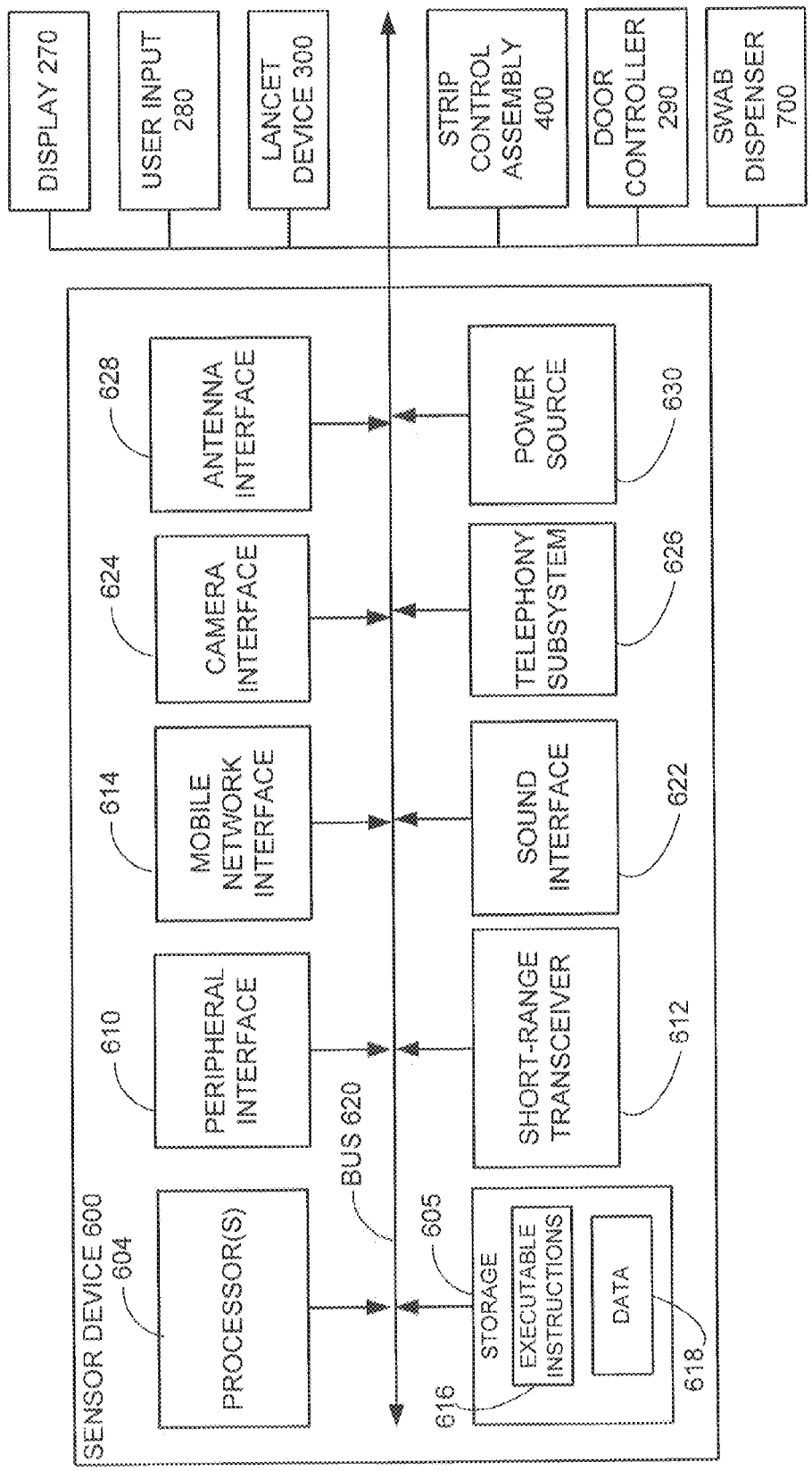
FIG. 12 is a system diagram of a sensor device and testing device components in accordance with an example implementation of the disclosed technology.

In accordance with the disclosed technology, the sensor device 600 performs the testing analysis on the fluid sample provided by a user onto a testing strip. Accordingly, the sensor device 600 may include one or more processors 604 operatively connected to a storage component 605, a bus 620 configured to facilitate communication between the various components of the sensor device 600, and a power source 630 configured to power one or more components of the sensor device 600. The power source may be configured to provide an appropriate alternating current (AC) or direct current (DC) to power components. In some implementations, as shown in FIG. 12, bus 620 is further configured to facilitate communication between the various components of the sensor device 600 and other components of testing device 100, such as user input device 280, display 270, lancet device 300, strip control assembly 400, door controller 290 and swab dispenser 700.

In example implementations of the disclosed technology, sensor device 600 includes any number of hardware and/or software applications that are executed to facilitate any of the fluid sampling operations described herein. In example implementations, one or more I/O interfaces facilitate communication between the testing device and one or more input/output devices. For example, one or more user interface devices, such as a display, keyboard, keypad, mouse, control panel, touch screen display, microphone, etc., may facilitate user interaction with the testing device. The one or more I/O interfaces may be utilized to receive or collect data and/or user instructions from a wide variety of input devices.

In further implementations, the sensor device 600 may further include a peripheral interface 610, a short-range transceiver 612, a mobile network interface 614 in communication with processor 604, a sound interface 622, a camera interface 624, a telephony subsystem 626, and an antenna interface 628. The sensor device 600 may be configured to use one or more input components via one or more of input/output interfaces (for example, peripheral interface 610, a short-range transceiver 612, a mobile network interface 614 in communication with processor 604, a sound interface 622, a camera interface 624, a telephony subsystem 626, and an antenna interface 628) to present information to a user, for example on display 270, or receive input from the user via display 270 or user input device 280. The short range transceiver 612 may be compatible with one or more of radio-frequency identification (RFID), near-field communication (NFC), Bluetooth®, low-energy Bluetooth® (BLE), WiFi™, ZigBee®, ambient backscatter communications (ABC) protocols or similar technologies. The mobile network interface 614 may include hardware, firmware, and/or software that allows the processor(s) 102 to communicate with other devices via wired or wireless networks, whether local or wide area, private or public, as understood by those of ordinary skill in the art. Received data may be processed by one or more computer processors as desired in various implementations of the disclosed technology and/or stored in one or more memory devices.

The processor 604 may include one or more of a microprocessor, microcontroller, digital signal processor, co-processor or the like or combinations thereof capable of executing stored instructions and operating upon stored data. The storage component 605 may include, in some implementations, one or more suitable types of memory (e.g. such as volatile or non-volatile memory, random access memory (RAM), read only memory (ROM), programmable read-only memory (PROM), erasable programmable read-only memory (EPROM), electrically erasable programmable read-only memory (EEPROM), magnetic disks, optical disks, floppy disks, hard disks, removable cartridges, flash memory, a redundant array of independent disks (RAID), and the like). The storage component may store files including an operating system, application programs (including, for example, a web browser application, a widget or gadget engine, and or other applications, as necessary), executable instructions 616 and data 618.

In some implementations, the input/output components described above may be integrated with the sensor device 600 architecture, or may be a separate component within testing device 100. As additional examples, input components may include an accelerometer, a magnetometer, a digital camera, a microphone, an infrared sensor, and an optical sensor.

While the sensor device 600 has been described as one form for implementing the techniques described herein, those having ordinary skill in the art will appreciate that other, functionally equivalent techniques may be employed. For example, in some implementations, the processing techniques described herein are implemented as a combination of executable instructions 616 and data 618 within the storage component 605. In addition, some or all of the functionality implemented via executable instructions 616 may also be implemented using firmware and/or hardware devices such as application specific integrated circuits (ASICs), programmable logic arrays, state machines, etc.

In some implementations, the user may utilize the user input device 280, or an application icon 285, to initiate a controlled process in which the testing device 100, in a automated fashion, uses components to move a testing strip onto the support member, prepare a cleansing swab from a swab dispenser, extend the lancet from the lancet device out of the housing, open the sample door for the user to provide the sample, analyze the sample, and provide the user with results through the user interface, and within its housing, move the used test strip from the second position into the disposal receptacle for later disposal by the user.

Figure 3:
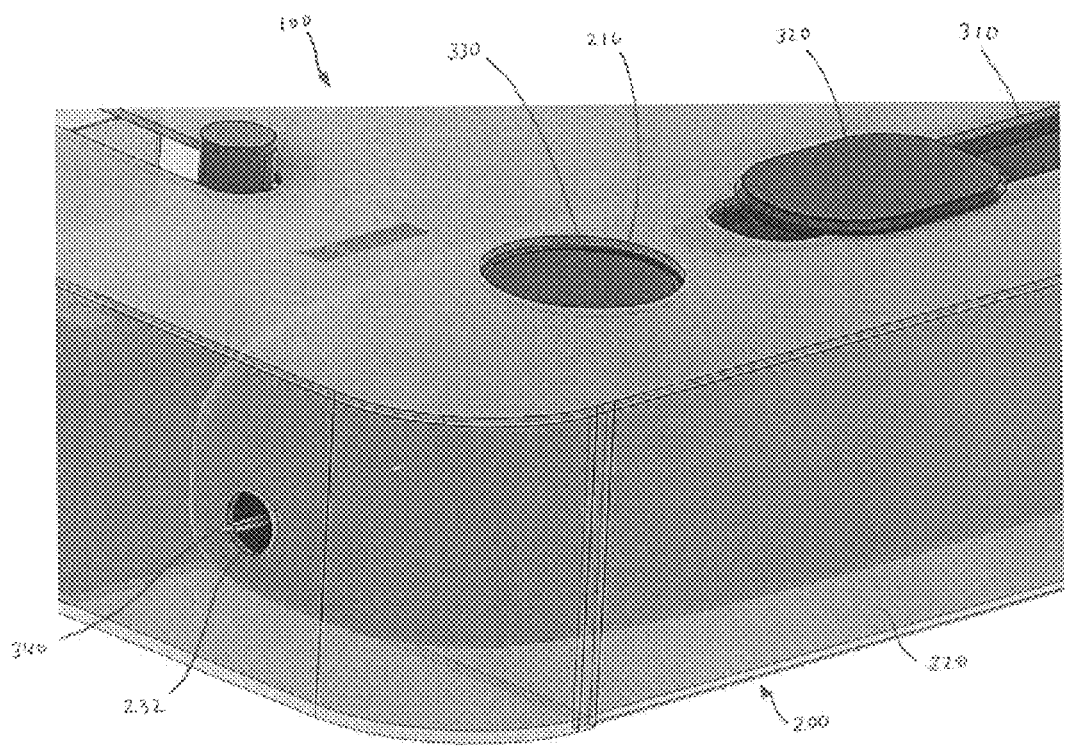
FIG. 3 is a partial perspective view of a fluid sample device in accordance with an example implementation of the disclosed technology.

FIG. 3 is a partial perspective view of a fluid sample device in accordance with an example implementation of the disclosed technology. As shown in FIG. 3, when the control button 330 is depressed, the lancet device 300 causes a lancet 340 loaded in the body 310 of the lancet device 300 to move axially from a retracted, resting position to an extended position where it extends through the lancet aperture 232 in housing 200 and can be used by the user to draw a fluid sample. For example, the user of the testing device 100 may press the control button 330 to extend the lancet 340 outside of the housing 200, and puncture her finger using the lancet 340 to draw a fluid sample that can be provided on a test strip within the testing device 100.

Figure 4:
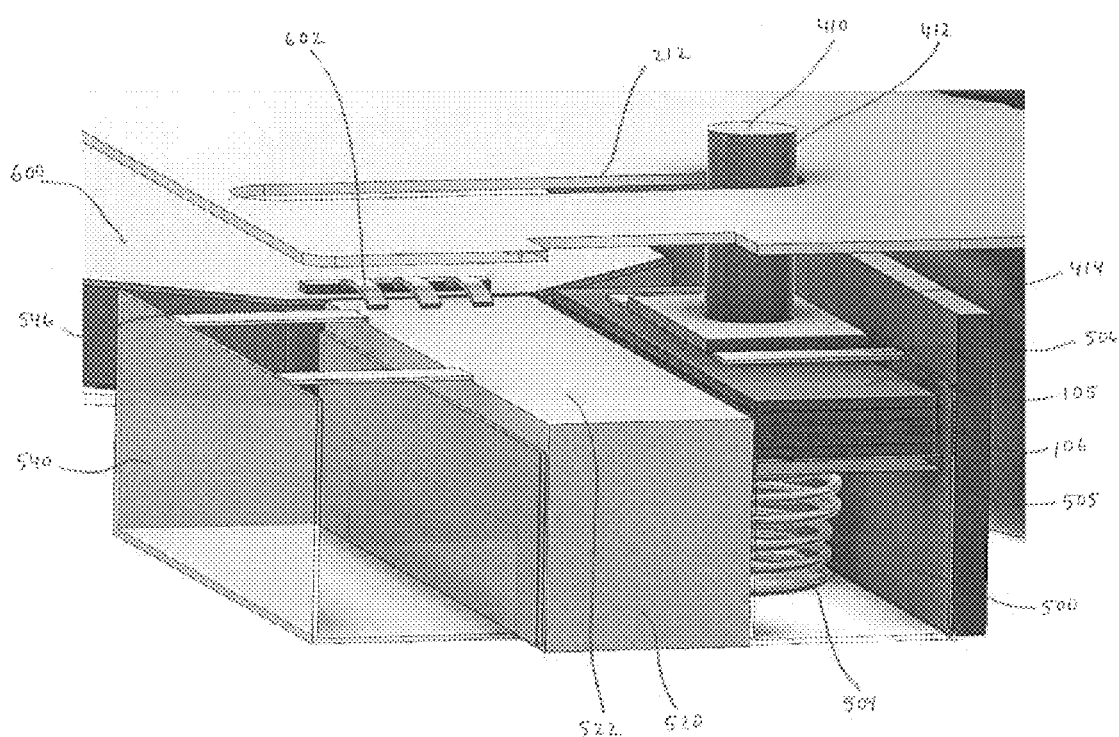
FIG. 4 is a partial perspective view of a fluid sample device, with a portion of the device housing not shown, holding a plurality of illustrative test strips, in accordance with an example implementation of the disclosed technology.

FIG. 4 is a partial perspective view of a fluid sample device with a portion of housing removed in accordance with an example implementation of the disclosed technology. In operation, the user of the testing device 100 must load testing strips 106 into the device 100 before it can be used for testing. As shown in FIG. 4, a plurality of illustrative test strips 106 have been inserted into the testing device 100 and loaded into the loading receptacle 500. As a test strip 106 is loaded, it slides under the guides 506 and forces the platform 505 down, which compresses the spring means 504. The spring mechanism 502 is configured to compress so that the loading receptacle 500 can receive a plurality of test strips 106, as shown above in FIG. 2. Test strip 105 is loaded in the first position on the top of the stack of loaded test strips 106. In some implementations, test strips 106 may be provided in a cartridge adapted to be loaded into the loading receptacle 500.

Figure 5:
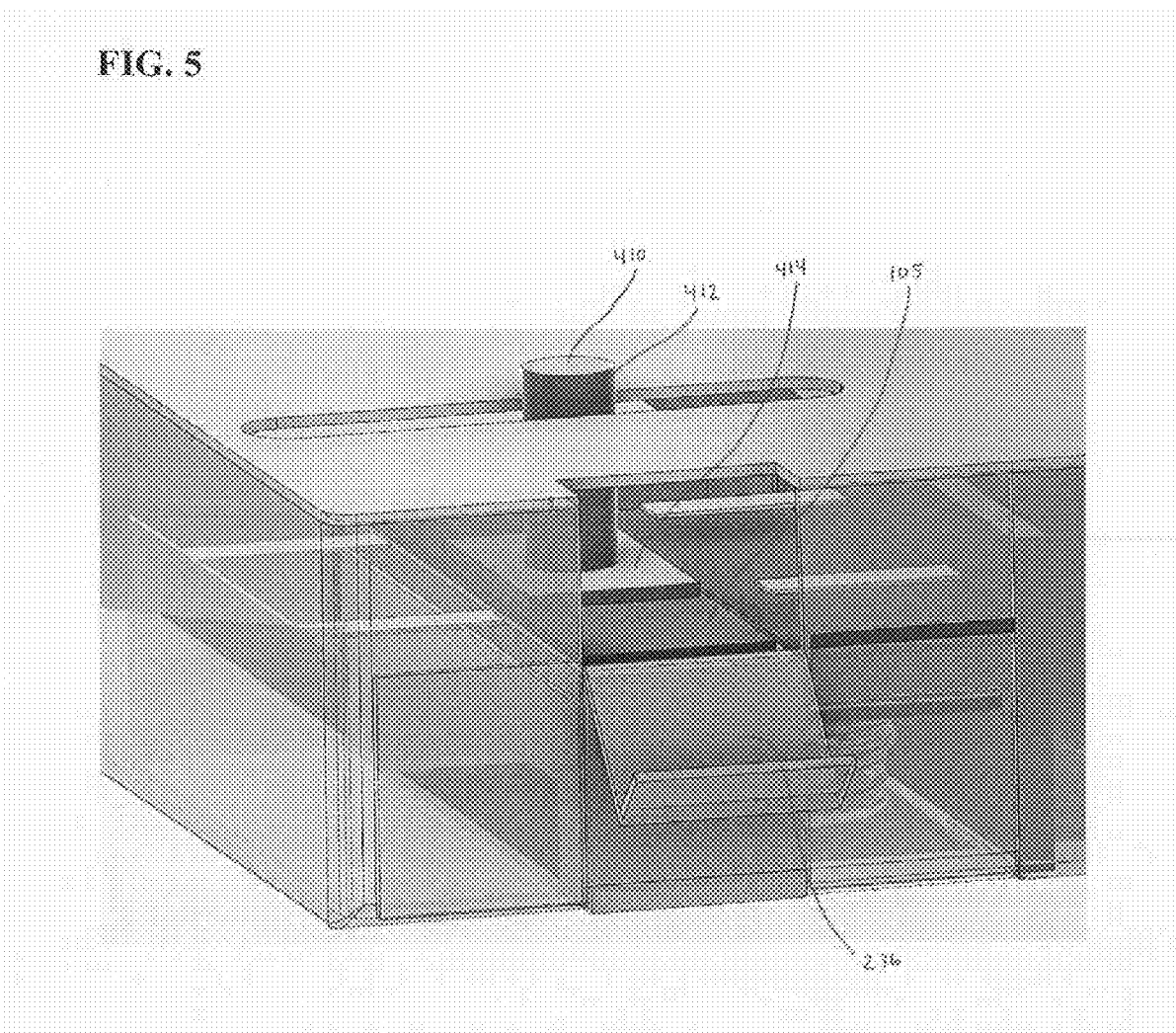
FIG. 5 is a partial perspective view of a fluid sample device with a sample door shown in an open position and making accessible an illustrative test strip disposed therein, in accordance with an example implementation of the disclosed technology.

FIG. 5 is a partial perspective view of a fluid sample device with a sample door shown in an open position and making accessible an illustrative test strip disposed therein in accordance with an example implementation of the disclosed technology. As shown in FIG. 5, test strip 105 has been moved to a second position on the platform 522 of support member 520. The test strip 105 can be accessed through the sample door 236, which is shown in an open position. In operation, a user can provide a fluid sample on the test strip 105 through the sample door 236.

Figure 6:
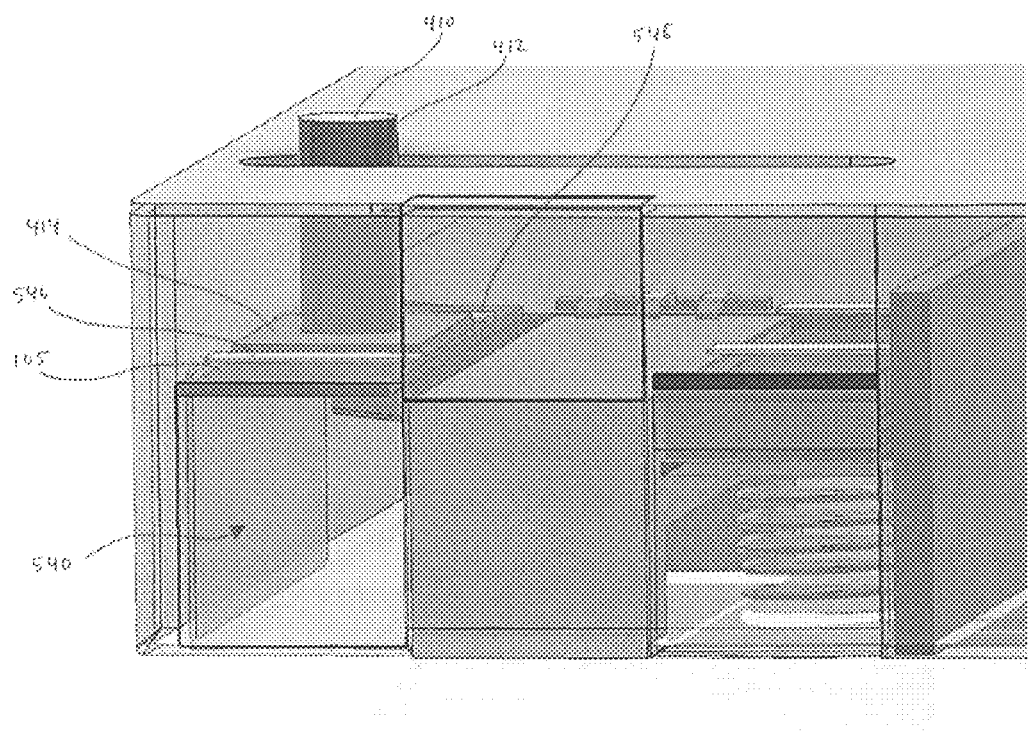
FIG. 6 is a partial perspective view of a fluid sample device with an illustrative test strip disposed therein, in accordance with an example implementation of the disclosed technology.
Figure 7:
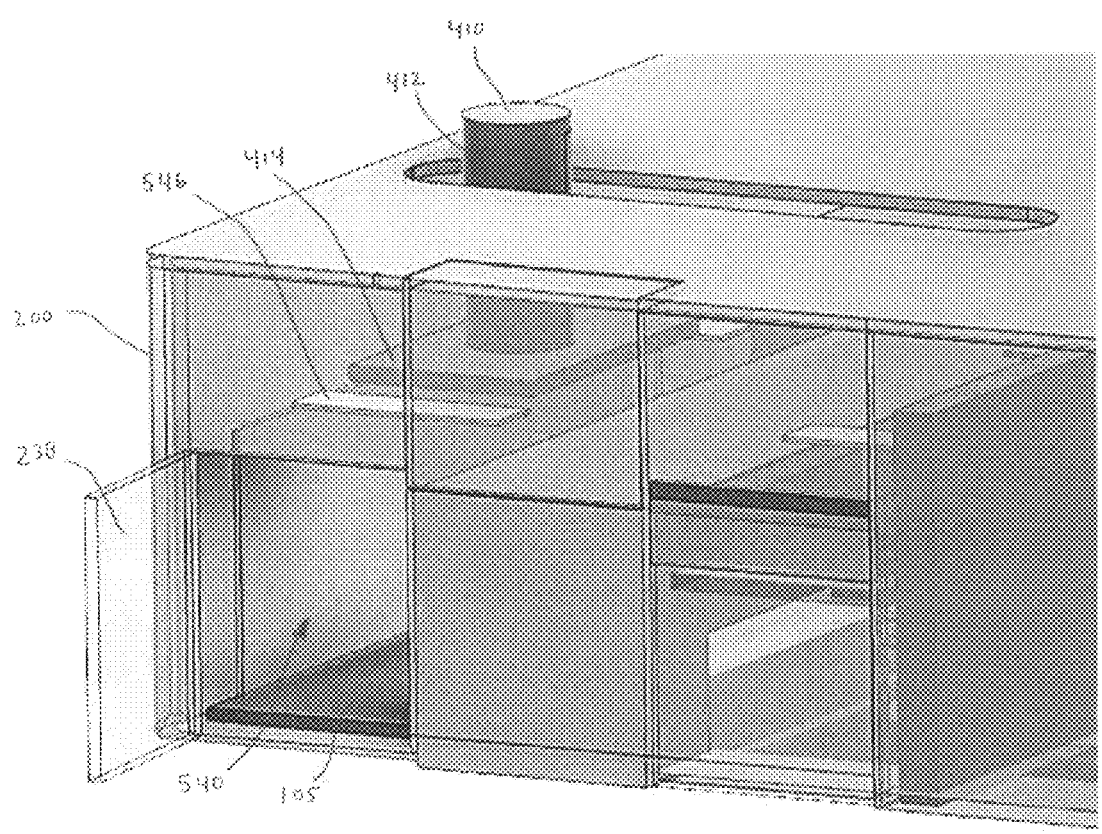
FIG. 7 is a partial perspective view of a fluid sample device with a disposal door shown in an open position and making accessible an illustrative test strip disposed therein, in accordance with an exemplary implementation of the disclosed technology.

FIG. 6 is a partial perspective view of a fluid sample device with an illustrative test strip disposed therein, in accordance with an example implementation of the disclosed technology. As shown in FIG. 6, when testing is complete, the user can move the used test strip over the disposal receptacle 540 into a third position using the control member 410. Once over the disposal receptacle 540, the user can releasably detach the used test strip from the control member 410, as shown in FIG. 7. The used test strip is stored in the disposal receptacle 540, and accessible through the disposal door 238 in the housing 200, which can be used to gain access to and remove the used test strip or strips.

Figure 8:
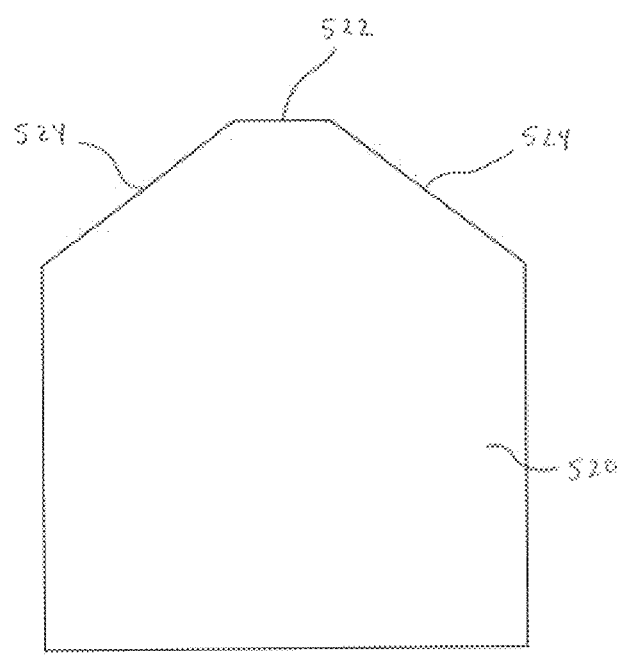
FIG. 8 is a partial perspective view of a fluid sample device, with a portion of the device housing not shown, in accordance with an example implementation of the disclosed technology.

FIG. 8 is a partial side view of a support member in accordance with an example implementation of the disclosed technology. As shown in FIG. 8, in some implementations, the support member 520 includes inclined edges 524 to bias a test strip being moved from the first position to the second position on the platform 522 of the support member 524.

Figure 9:
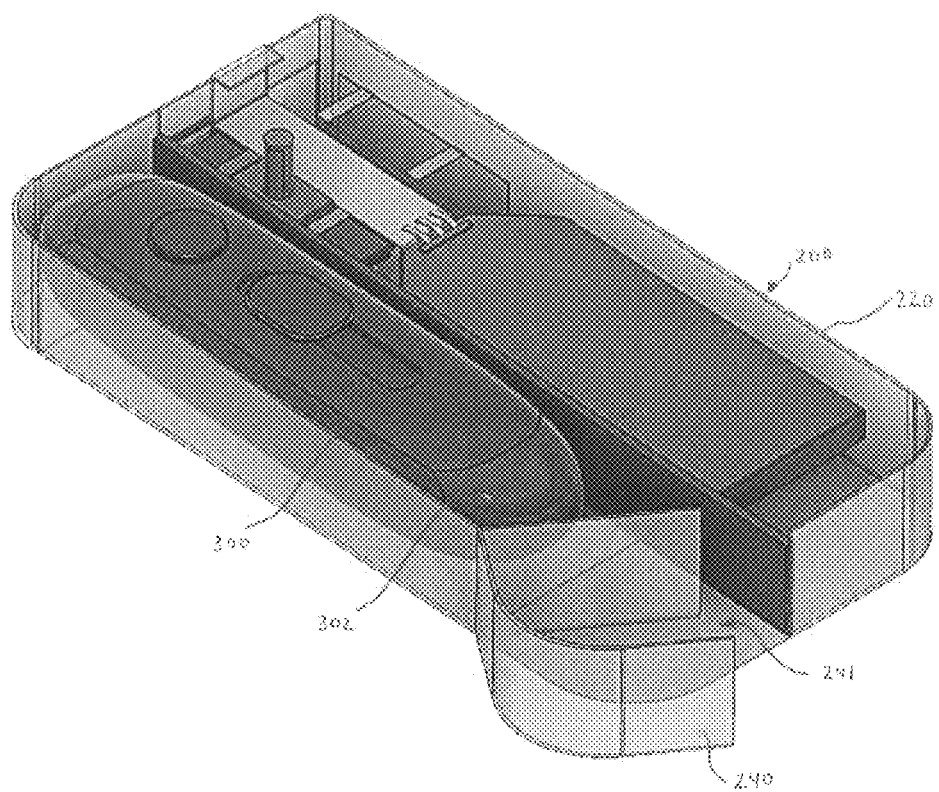
FIG. 9 is a perspective view of a fluid sample testing device with a lancet loading door shown in an open position and with a portion of the device housing not shown, in accordance with an example implementation of the disclosed technology.

FIG. 9 is a perspective view of a fluid sample testing device with a lancet loading door shown in an open position and with a portion of the device housing not shown, in accordance with an example implementation of the disclosed technology. As shown in FIG. 9, in some implementations, a lancet loading door 240 in hingedly mounted to the bottom portion 220 of housing 200 so that the user may open the door to gain access to the rear 302 of the lancet device 300 and load additional lancets into the lancet device 300, as will be understood by those of skill in the art. In some implementations, the lancets may be loaded as individual lancets or within a cartridge containing a plurality of lancets configured to cooperate with the lancet device to load individual lancets using the charging mechanism. In some implementations, the housing 200 includes an interior area 241 exposed by lancet loading door 240 to store extra components, such as replacement lancets or lancet cartridges, testing strips or testing strip cartridges, cleansing swabs or swab rolls.

Figure 10:
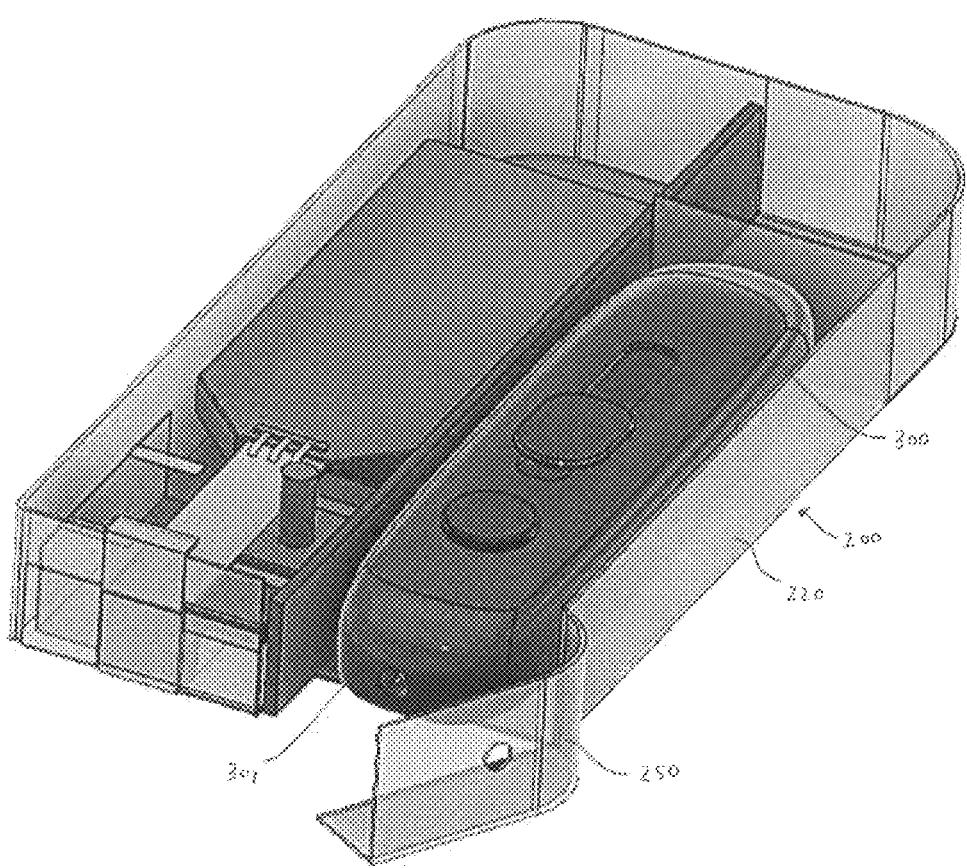
FIG. 10 is a perspective view of a fluid sample testing device with a lancet removal door shown in an open position and with a portion of the device housing not shown, in accordance with an example implementation of the disclosed technology.

FIG. 10 is a perspective view of a fluid sample testing device with a lancet removal door shown in an open position and with a portion of the device housing not shown, in accordance with an example implementation of the disclosed technology. As shown in FIG. 10, a lancet removal door 250 is hingedly mounted to the housing 200 so that the user may open the door to gain access to the front 301 of the lancet device 300 and remove used lancets from the lancet device 300, as will be understood by those of skill in the art.

Figure 11:
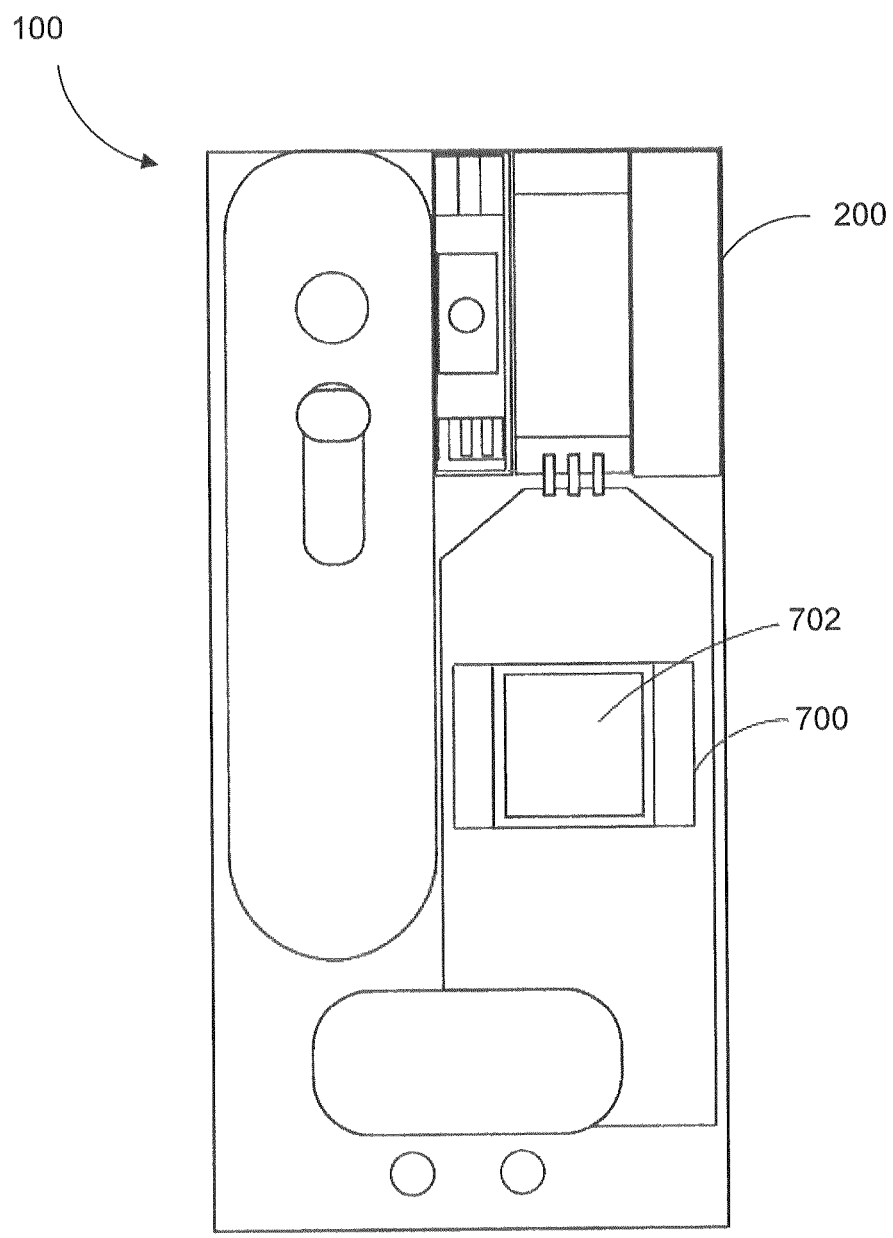
FIG. 11 is a top view of a fluid sample testing device in accordance with an example implementation of the disclosed technology.

FIG. 11 is a top view of a fluid sample testing device in accordance with an example implementation of the disclosed technology. As shown in FIG. 11, in some implementations, the testing device includes a swab dispenser apparatus 700 mounted primarily within the housing. The swab dispenser 700 can be loaded with a plurality of cleansing swabs 702, such as alcohol swabs, releasably attached on a swab roll. The swab dispenser 700 retains the unused cleansing swabs within the housing until needed by the user for use in the fluid testing process. A user can obtain an unused cleansing swab from the swab dispenser when needed to clean a puncture site to draw a fluid sample. This is important because the cleanliness of the area from which the fluid sample, such as a blood sample, will be drawn can have a notable effect on the analysis test result. In some implementations, a user pulls on an exposed portion of an unused swab loaded in the swab dispenser and pulls the full unused swab from within the housing to the outside of the device. Once the user is finished with the exposed cleansing swab, it can be separated from the roll of unused swabs along a tear line as will be understood by those of ordinary skill in the art. In some implementations, the testing device allows for the containment and unwrapping of alcohol swabs, and holding of the wrapper until it can be disposed of at a later time.

FIG. 13 is a flow diagram of a method 800 of using a testing device in accordance with an example implementation of the disclosed technology. The method 800 begins when a user provides an input command to initiate a fluid sampling or testing process in 802. In some implementations, the user may utilize the user input device 280, or an application icon 285, to provide the input command. After receiving the input command, the testing device 100, in a automated fashion, in 804 causes the strip control assembly 400 to move a testing strip from the first position in the loading receptacle 500 onto the support member 520 in the second position. In 806, the testing device 100 initiates a door controller 290 to open the sample door 236 for the user to provide a fluid sample on the test strip in the second position. In 808, the testing device 100 causes the swab dispenser 700 to prepare a cleansing swab for the user. In 810, the testing device 100 causes the lancet device 300 to extend the lancet 340 out of the housing 200 for the user to prick the tissue area and draw the sample. In 812, the testing device 100 causes the sensor device 600 to analyze the received sample. In 814, the testing device 100 causes the results of the testing to be displayed on the display 270. In 816, the testing device 100, within its housing, causes the strip control assembly 400 to move the used test strip from the second position to the third position in the disposal receptacle for later disposal by the user.

As seen herein, the disclosed technology reduces the struggle that currently available testing devices create. Existing testing devices are bulky and make the testing process both uncomfortable and time consuming. The disclosed technology provides the functionality of the existing testing kits into one discrete, compact device, and allows for hands-free mounting and disposal of testing strips. The automation of the testing strip loading, preparation, and disposal reduces the amount of contact between the user and test strips, which in turn, produces a more sanitary test strip. This also produces more accurate testing results because the accuracy of the blood glucose reading is based on the quality of the blood sample and the state of the testing strip. Moreover, the state of the area from which blood is drawn, whether clean or dirty, can affect the results of the blood glucose analysis. Overall, the testing device lowers the risk that the blood sample on the test strip can be impacted by any foreign substances by minimizing the amount of user-strip contact needed for testing.

In addition to an increase in the cleanliness in of the testing process, the automation of the test strip insertion, preparation and disposal process in the disclosed technology drastically reduces the time that the user spends performing the complete testing process. The disclosed technology enables the user to no longer have to struggle to retrieve a single test strip from a small container of several tightly packed test strips. This is especially important when the user needs to conduct testing and may be suffering from hypoglycemia, which involves common symptoms such as shakiness, confusion, and dizziness. These symptoms can make it very difficult to get hold of a test strip and to accurately insert it into a blood glucose meter. The disclosed technology not only makes the process easier for the user during a hypoglycemic event but in any other situation where the user is not perfectly stable or focused, such as while walking or even while riding as a passenger in a car.

In current testing kits, the retrieval of a test strip from the test strip container and the insertion of that test strip into the blood glucose meter is typically a two-handed process in which the meter must be set down on a surface. This is a large inconvenience to the user because all other actions must be stopped and a suitable place to set materials down must be found. Using the disclosed technology, the user completes the testing process conveniently, discreetly, and time effectively, and in some cases, with the use of only one hand.

The design and functionality described in this application is intended to be exemplary in nature and is not intended to limit the instant disclosure in any way. Those having ordinary skill in the art will appreciate that the teachings of the disclosure may be implemented in a variety of suitable forms, including those forms disclosed herein and additional forms known to those having ordinary skill in the art. For example, one skilled in the art will recognize that executable instructions may be stored on a non-transient, computer-readable storage medium, such that when executed by one or more processors, causes the one or more processors to implement the testing method described above.

In this description, numerous specific details have been set forth. It is to be understood, however, that implementations of the disclosed technology may be practiced without these specific details. In other instances, well-known methods, structures and techniques have not been shown in detail in order not to obscure an understanding of this description. References to "one implementation," "an implementation," "example implementation," "various implementations," "some implementations," etc., indicate that the implementation(s) of the disclosed technology so described may include a particular feature, structure, or characteristic, but not every implementation necessarily includes the particular feature, structure, or characteristic. Further, repeated use of the phrase "in one implementation" does not necessarily refer to the same implementation, although it may.

Throughout the specification and the claims, the following terms take at least the meanings explicitly associated herein, unless the context clearly dictates otherwise. The term "connected" means that one function, feature, structure, or characteristic is directly joined to or in communication with another function, feature, structure, or characteristic. The term "coupled" means that one function, feature, structure, or characteristic is directly or indirectly joined to or in communication with another function, feature, structure, or characteristic. The term "or" is intended to mean an inclusive "or." Further, the terms "a," "an," and "the" are intended to mean one or more unless specified otherwise or clear from the context to be directed to a singular form. By "comprising" or "containing" or "including" is meant that at least the named element, or method step is present in article or method, but does not exclude the presence of other elements or method steps, even if the other such elements or method steps have the same function as what is named.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

Certain implementations of the disclosed technology are described above with reference to block and flow diagrams of systems and methods and/or computer program products according to example implementations of the disclosed technology. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, may be repeated, or may not necessarily need to be performed at all, according to some implementations of the disclosed technology.

While certain implementations of this disclosure have been described in connection with what is presently considered to be the most practical and various implementations, it is to be understood that this disclosure is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the technology and also to enable any person skilled in the art to practice certain implementations of this technology, including making and using any apparatuses or systems and performing any incorporated methods. The patentable scope of certain implementations of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Exemplary Use Case

The following exemplary use case describes one example of a typical user flow pattern. It is intended solely for explanatory purposes and not in limitation. In this example, the user will determine that it is necessary to test the glucose level in her blood. The user will retrieve the testing device in accordance with the disclosed technology. The user will use the strip control assembly to move a testing strip into a sample position within the housing of the testing device. The user will expose an unused cleansing swab from the swab dispenser to cleanse the tissue area from which the fluid sample will be drawn. The user will then determine if a lancet has been loaded into the lancet device. If so, the user can depress the lancet control button to force the lancet from the lancet device into an extended position that extends outside of the testing device housing. The user can place her tissue area onto the exposed lancet to draw the fluid sample. The user can then access the testing strip in the second position through the sample door in the housing. The user can deposit the fluid sample on the testing strip. The fluid sample disperses on the testing strip, and the sensor device, which is operatively engaged with the testing strip gathers data from the testing strip. The sensor device analyzes data regarding the fluid sample, and communicates data for display to user on a user interface. Once testing is complete, the user can utilize the strip control assembly to move the used testing strip from the second position to a third position in a disposal receptacle within the housing. The used testing strip can remain in the disposal receptacle until it is convenient for the user to discard it. The user can access the used testing strip through a disposal door in the housing to remove it for disposal.

Another exemplary use case can automate some or most of the above procedures for an even more simplified and hands-free process. The user can initiate the process which can then follow the above sequence of events, interspersed with time delays, to allow the user to act. Alternately, the automated system can wait for physical cues to trigger the next event. As an example, the user can depress a user input device 280 or application icon 285 to begin the sequence. The first portion of the sequence can replace the actions of the user actuating the lancet control button 330. Wherein the device loads a lancet and signals the user to place her body tissue to be puncture to draw a fluid sample that can then be analyzed in the testing device 100. The signal to the user can be audio, visual, or tactile. In one example the signals are vibrations to silently notify the user of each stage in the sequence. Once the lancet is discharged, the automated process moves a test strip into the sensing device and again signals the user to provide the fluid for the sampling. Once the sensing device competes its reading of the fluid sample, the sequence automatically removes the test strip and deposits it in the disposal receptacle. An alcohol swab can also be automatically discharged once the test results are complete, or at a set time after the test strip is moved into testing position.

Further signals to the user can also note the testing interval, i.e. when it is time for the user to take a sample. As above, the signal can be audio, visual, or tactile. In one example the signals are vibrations to silently notify the user of the appropriate time. The processor 604 can be programmed with the user's specific intervals, or be preprogrammed for known intervals based on typical sampling regiments. Alternately, the signal can be generated from a notification sent from an external device linked to the testing device 100 through one or more interfaces 610, 612, 614, 626, 628.

Importantly, the testing device provides a single, handheld testing device that allows the user to complete the testing process without having to handle several separate physical items, which results in a more sanitary and accurate testing process.

The invention claimed is:

1. A device for facilitating a testing of a fluid sample on a test strip, comprising:
   a housing containing a loading receptacle, a support member, a disposal receptacle, a lancet device and a sensor device, the loading receptacle adapted to receive the test strip, the support member adapted to support the test strip, the disposal receptacle adapted to hold the test strip, the sensor device adapted to analyze the fluid sample; and
   a strip control assembly adapted to contact and move the test strip from a first position in the loading receptacle to a second position operatively engaged with the sensor device, and from the second position to a third position in the disposal receptacle,
   wherein the strip control assembly is adapted to move the test strip in a single linear direction from the first position to the second position and the single direction from the second position to the third position, and
   wherein as the strip control assembly moves the test strip from the first position to the second position, the entire strip control assembly is configured to exit a first location and enter a second location, wherein as the strip control assembly moves the test strip from the second position to the third position, the entire strip control assembly is configured to exit the second location and enter a third location.

2. The device of claim 1, further comprising a sample door mounted on the housing to provide access to the test strip in the second position.

3. The device of claim 1, further comprising a lancet adapted to puncture skin,
   wherein the lancet device is adapted to receive the lancet, and move the lancet from a retracted position to an extended position in which a portion of the lancet extends outside of the housing.

4. The device of claim 1, wherein the lancet device is adapted to receive a lancet in a lancet cartridge.

5. The device of claim 1, further comprising a loading door mounted on the housing to load the test strip in the loading receptacle.

6. The device of claim 1, further comprising a disposal door mounted on the housing to provide access to the test strip in the disposal receptacle.

7. The device of claim 1, the strip control assembly comprising a control member disposed partially within the housing, the control member adapted to releasably engage the test strip in the first position.

8. The device of claim 7, further comprising an adhesive disposed on a contact portion of the control member, the adhesive for releasably engaging the test strip.

9. The device of claim 1, further comprising a platform and a spring adapted to force the test strip in the first position.

10. The device of claim 1, further comprising a guide adapted to retain the test strip in the first position in the loading receptacle.

11. The device of claim 1, further comprising a guide mounted above the disposal receptacle.

12. The device of claim 1, wherein the loading receptacle is adapted to receive the test strip in a test strip cartridge configured to hold a plurality of test strips.

13. The device of claim 1, further comprising a processor that generates a notification signal at at least one of a certain interval and an event.

14. A device for facilitating a testing of a fluid sample on a test strip, comprising:
 a housing comprising:
 a loading receptacle adapted to receive the test strip in a first position;
 a support member adapted to support the test strip in a second position;
 a disposal receptacle adapted to hold the test strip in a third position;
 a lancet adapted to puncture skin;
 a lancet device adapted to receive the lancet, and move the lancet from a retracted position to an extended position in which a portion of the lancet extends outside of the housing;
 a sensor device adapted to analyze the fluid sample;
 a strip control assembly comprising a control member, the control member disposed partially within the housing, the control member adapted to contact and move the test strip from the first position to the second position in a single linear direction and to contact and move the test strip from the second position to the third position in the same single linear direction, wherein as the control member moves the test strip between the first and second positions, the entire control member is configured to exit a first location and enter a second location, and wherein as the control member moves the test strip between the second and third positions, the entire control member is configured to exit the second location and enter a third location;
 a loading door in the housing to load the test strip into the housing;
 a sample door in the housing to access the test strip in the second position; and
 a disposal door in the housing to access the test strip in the third position;
 wherein, in the second position, the test strip is accessible through the sample door to receive the fluid sample, and the test strip is operatively engaged with the sensor device.

15. A method of testing a fluid sample on a test strip using a testing device, the testing device including a loading receptacle, a support member, a disposal receptacle, a lancet device and a sensor device contained within a housing, and a strip control assembly, the method comprising:
 contacting and moving, using the strip control assembly, the test strip from a first position in the loading receptacle to a second position;
 depositing the fluid sample on the test strip for testing by the sensor device, the sensor device operatively engaged with the test strip in the second position; and
 moving, with the strip control assembly, the test strip from the second position to a third position in the disposal receptacle when the testing is completed,
 wherein both moving steps are performed in the same linear direction such that the entire test strip control assembly exits a first location and enters a second location as the strip control assembly moves the test strip from the first position to the second position and the entire test strip assembly exits the second location and enters a third location as the strip control assembly moves the test strip from the second position to the third position.

16. The method of claim 15, further comprising the step of generating a notification signal using a processor.

* * * * *